(12) United States Patent
King (10) Patent No.: US 9,707,072 B2
(45) Date of Patent: Jul. 18, 2017

(54) ASSEMBLY OF STENT GRAFTS WITH DIAMETER REDUCING TIES

(71) Applicant: Cook Medical Technologies LLC, Bloomington, IN (US)

(72) Inventor: Chantelle King, Woodridge (AU)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 189 days.

(21) Appl. No.: 14/555,012

(22) Filed: Nov. 26, 2014

(65) Prior Publication Data
US 2015/0082595 A1 Mar. 26, 2015

Related U.S. Application Data

(62) Division of application No. 13/795,088, filed on Mar. 12, 2013, now Pat. No. 8,926,686.

(30) Foreign Application Priority Data

Nov. 27, 2012 (AU) ................................ 2012258395

(51) Int. Cl.
*A61F 2/07* (2013.01)
*A61F 2/852* (2013.01)
(Continued)

(52) U.S. Cl.
CPC ................ *A61F 2/07* (2013.01); *A61F 2/852* (2013.01); *A61F 2002/061* (2013.01);
(Continued)

(58) Field of Classification Search
CPC ..................................... A61F 2/06; A61F 2/07
(Continued)

(56) References Cited

U.S. PATENT DOCUMENTS 6,471,722 B1 10/2002 Inoue
6,485,515 B2* 11/2002 Strecker ................... A61F 2/04
606/194

(Continued)

FOREIGN PATENT DOCUMENTS

WO        9853761     12/1998
WO        2008140796  11/2008

OTHER PUBLICATIONS

European Search Report, 13275207.2-1651, Cook Medical Technologies LLC, Jan. 29, 2014.

*Primary Examiner* — Suzette J Gherbi
(74) *Attorney, Agent, or Firm* — Brinks Gilson & Lione (57) ABSTRACT

A temporary diameter reduction constraint arrangement for a stent graft is disclosed. The arrangement comprises: primary and secondary release wires extending along the graft; a plurality of loops of thread, each loop engaged with either the primary or secondary wire and engaged around a portion of the graft circumferentially spaced away from its release wire, and drawn tight to reduce the diameter of the graft; an end constraint arrangement comprising four of the plurality of loops of thread arranged into a first and second pairs engaged with respective primary and secondary wires; and an intermediate constraint arrangement comprising a fifth and sixth of the plurality of loops of thread arranged into a third pair, the third pair engaged with the primary release wire, the primary release wire deviating towards the secondary release wire so as to locate the intermediate constraint arrangement substantially in-line with the end constraint arrangement.

20 Claims, 8 Drawing Sheets

(51) Int. Cl.
*A61F 2/06* (2013.01)
*A61F 2/95* (2013.01)

(52) U.S. Cl.
CPC ............. *A61F 2002/9511* (2013.01); *A61F 2220/0075* (2013.01); *A61F 2240/001* (2013.01); *A61F 2250/001* (2013.01); *Y10T 29/49716* (2015.01)

(58) Field of Classification Search
USPC ................................................ 623/1.1–1.36
See application file for complete search history.

(56) References Cited

U.S. PATENT DOCUMENTS

| | | | |
|---|---|---|---|
| 6,878,161 B2 | 4/2005 | Lenker | |
| 8,377,113 B2* | 2/2013 | Hartley | ............... A61F 2/07 623/1.23 |
| 2006/0004433 A1 | 1/2006 | Greenberg et al. | |
| 2007/0043425 A1 | 2/2007 | Hartley et al. | |
| 2011/0264192 A1* | 10/2011 | Hartley | ............... A61F 2/07 623/1.13 |

* cited by examiner

ASSEMBLY OF STENT GRAFTS WITH DIAMETER REDUCING TIES

CROSS REFERENCE TO RELATED APPLICATIONS

This application is a divisional of U.S. patent application Ser. No. 13/795,088 filed on Mar. 12, 2013 entitled "Assembly of Stent Grafts with Diameter Reducing Ties", the entire contents of which is incorporated herein by reference, and claims priority from Australian patent application serial no. 2012258395 filed on Nov. 27, 2012 entitled "Assembly of Stent Grafts with Diameter Reducing Ties" the contents of which are incorporated in their entirety herein and for all purposes.

FIELD OF INVENTION

This invention relates to a medical device and more particularly to a stent graft for mounting onto a deployment device for endovascular introduction.

BACKGROUND OF THE INVENTION

This invention will be particularly discussed in relation to stent grafts for placement into the thoracic abdominal aorta or into the abdominal aorta for the treatment of aneurysms. The invention, however, is not so restricted and may be applied to stent grafts for placement in any lumen of the human or animal body.

The positioning of stent grafts is very important for a number of reasons including in many cases the need to avoid occlusion of branch arteries. Positioning is complicated however because the diameter of a stent graft is deliberately made larger than the diameter into which it is to be placed to allow for accurate sealing against the vessel wall, possible errors in sizing and subsequent relaxation of the vessel wall.

Once released from a delivery device, a stent graft with self-expanding stents will take up apposition against the vessel wall and it will be difficult if not impossible to reposition it. This can be dangerous if, for instance, renal arteries are occluded.

Stent graft assemblies with diameter reducing ties have been developed to assist surgeons with the task of positioning stent grafts after initial release from a deployment device. Sewing and positioning of such ties during manufacture can be difficult and time consuming. Furthermore, errors in this process can have adverse effects.

It is an object of the invention to address difficulties described above while at the same time improving safety and simplifying assembly or to at least provide a useful alternative assembly technique.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form the invention is said to reside in temporary diameter reduction constraint arrangement for a stent graft in combination with a stent graft, the stent graft having a proximal end and a distal end and comprising a biocompatible graft material tube and a plurality of longitudinally spaced apart self-expanding stents fastened thereto, including at least an end stent and a plurality of intermediate stents, the constraint arrangement comprising:

a primary release wire extending longitudinally along the graft material tube;

a secondary release wire extending longitudinally along the graft material tube;

a plurality of loops of thread, each loop engaged with one or other of the primary and secondary release wires and engaged around a portion of the stent graft circumferentially spaced a selected distance away from its release wire, and drawn tight and tied to itself to reduce the stent graft;

an end constraint arrangement comprising four of the plurality of loops of thread arranged into a first pair and second pair, the first pair engaged with the primary release wire and the second pair engaged with the secondary release wire; and an intermediate constraint arrangement comprising a fifth and sixth of the plurality of loops of thread arranged into a third pair, the third pair engaged with the primary release wire, the primary release wire deviating towards the secondary release wire.

In one form the temporary diameter reduction constraint arrangement comprises a plurality of intermediate constraint arrangements, each constraint arrangement comprising pairs of loops of thread engaged with the primary release wire.

In one form the secondary release wire deviates towards the primary release wire.

In one form the primary release wire deviates towards the secondary release wire.

In one form the deviation of the primary and secondary release wires toward each other is symmetrical.

In one form the end constraint arrangement constrains a sealing stent at the proximal end of the stent graft.

In one form the arrangement comprises a distal end constraint arrangement, the distal end constraint arrangement substantially in-line with the intermediate constraint arrangement.

In one form the stents are zig-zag stents comprising struts and bends there-between and each loop of thread engages around a strut.

In one form the end stent is non-super elastic.

In one form the intermediate stents are super elastic.

In another form the invention is said to reside in an expandible stent graft having a proximal end and a distal end, the stent graft comprising a biocompatible graft material tube having a sealing zone at the proximal end and a plurality of longitudinally spaced apart self-expanding stents, including at least an end stent and a plurality of intermediate stents, the end stent attached to an internal wall of the graft material tube, the stent graft including a constraint arrangement comprising:

a primary release wire extending longitudinally along the graft material tube;

a secondary release wire extending longitudinally along the graft material tube;

a plurality of loops of thread, each loop engaged with one or other of the primary and secondary release wires and engaged around a portion of the stent graft circumferentially spaced a selected distance away from its release wire, and drawn tight and tied to itself to reduce the stent graft;

an end constraint arrangement comprising four of the plurality of loops of thread arranged into a first pair and second pair, the first pair engaged with the primary release wire and the second pair engaged with the secondary release wire; and an intermediate constraint arrangement comprising a fifth and sixth of the plurality of loops of thread arranged into a third pair, the third pair engaged with the primary release wire, the primary release wire deviating towards the secondary release wire.

In one form the stent graft comprises a plurality of intermediate constraint arrangements, each constraint arrangement comprising pairs of loops of thread engaged with the primary release wire.

In one form the secondary release wire deviates towards the primary release wire.

In one form the primary release wire deviates towards the secondary release wire.

In one form the deviation of the primary and secondary release wires toward each other is symmetrical.

In one form the stent graft comprises a distal end constraint arrangement, the distal end constraint arrangement substantially in-line with the intermediate constraint arrangement.

In one form the stents are zig-zag stents comprising struts and bends there-between and each loop of thread engages around a strut.

In one form the end stent is non-super elastic.

In one form the intermediate stents are super elastic.

In another form the invention is said to reside in a method of temporarily reducing the diameter of at least a portion of a self-expanding stent graft, the stent graft having a proximal end and a distal end and comprising a biocompatible graft material tube and a plurality of longitudinally spaced apart self-expanding stents fastened thereto, including at least an end stent and a plurality of intermediate stents, the method comprising the steps of:

(a) securing a primary release wire longitudinally along the stent;

(b) securing a secondary release wire longitudinally along the stent graft;

(c) tying an end constraint arrangement comprising four loops of thread arranged into a first pair and second pair, the first pair engaged with the primary release wire and the second pair engaged with the secondary release wire; and (d) tying an intermediate constraint arrangement comprising two loops of thread arranged into a third pair, the third pair engaged with the primary release wire, wherein, the primary release wire deviates towards the secondary release.

In one form the method comprises the step of:

tying a plurality of intermediate constraint arrangements, each intermediate constraint arrangement comprising two loops of thread arranged into pairs, the pairs engaged with the primary release wire, so as to compress the stent graft along an entire length of the stent graft.

In one form the securing steps comprise threading the release wires through the graft material tube.

A detailed description of one or more embodiments of the invention is provided below along with accompanying figures that illustrate by way of example the principles of the invention. While the invention is described in connection with such embodiments, it should be understood that the invention is not limited to any embodiment. On the contrary, the scope of the invention is limited only by the appended claims and the invention encompasses numerous alternatives, modifications and equivalents. For the purpose of example, numerous specific details are set forth in the following description in order to provide a thorough understanding of the present invention.

The present invention may be practiced according to the claims without some or all of these specific details. For the purpose of clarity, technical material that is known in the technical fields related to the invention has not been described in detail so that the present invention is not unnecessarily obscured.

BRIEF DESCRIPTION OF THE DRAWINGS

This then generally describes the invention but, to assist with understanding, reference will now be made to the accompanying drawings which show preferred embodiments of the invention.

In the drawings:

FIG. 3 shows a stage in the construction of the first embodiment of the invention as shown in FIG. 2a;

DESCRIPTION OF PREFERRED EMBODIMENTS

Figure 1:
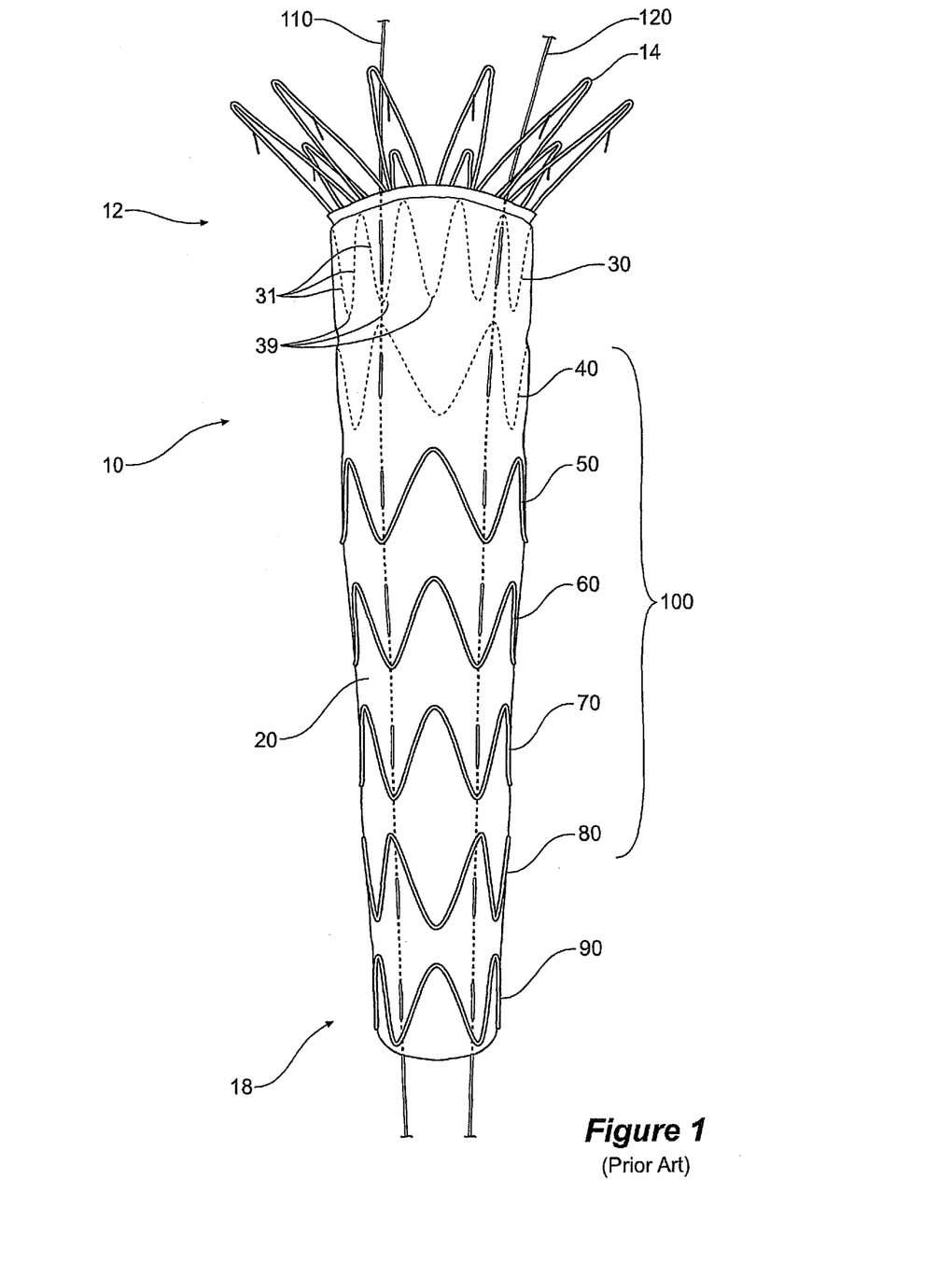
FIG. 1 shows a stent graft according to the prior art.

Referring to FIG. 1, a stent graft of the type shown in U.S. patent application Ser. No. 11/507,115 titled "Assembly of Stent Grafts" is shown. This stent graft 10 has release wires 110 and 120 that can be used together with reducing ties to achieve a reduction in the circumference of the stent graft 10 as is explained in the specification of the aforementioned U.S. patent application Ser. No. 11/507,115 titled "Assembly of Stent Grafts" which is hereby incorporated in its entirety into this specification.

Figure 2A:
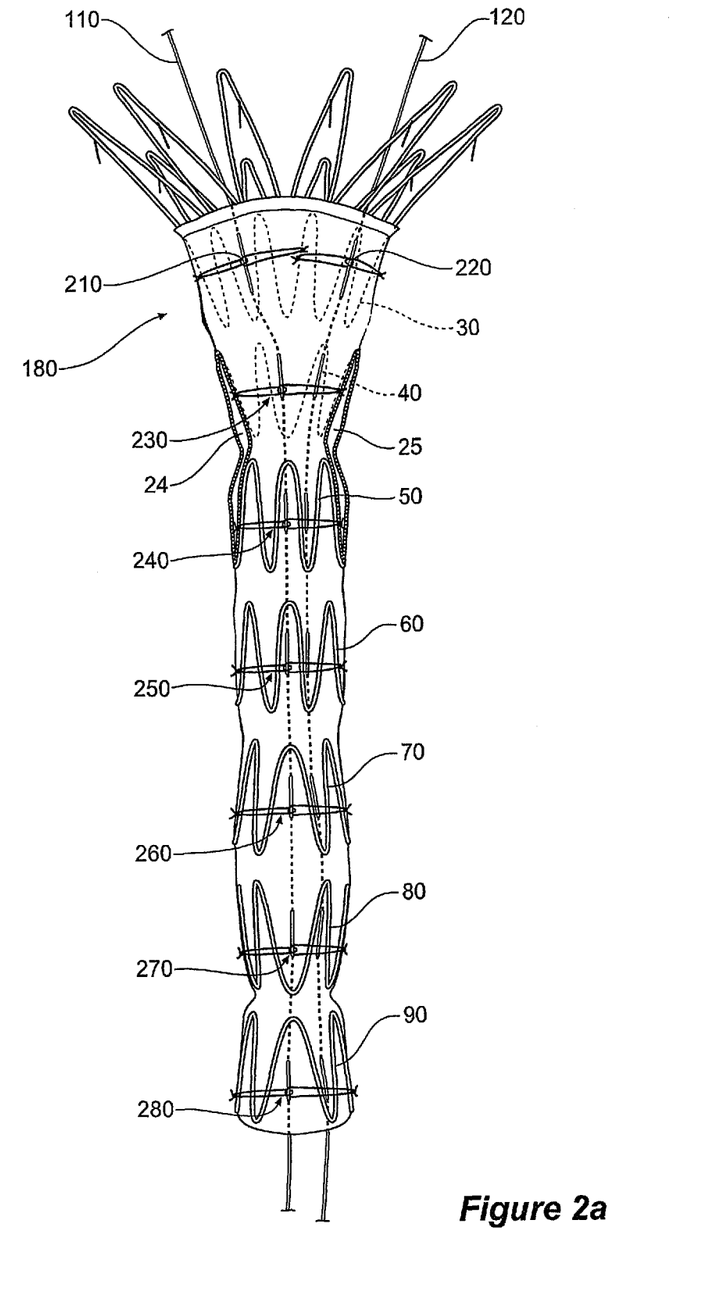
FIG. 2a shows a temporary diameter reduction constraint arrangement for a stent graft in combination with a stent graft according to a first embodiment of the invention in a front view.
Figure 2B:
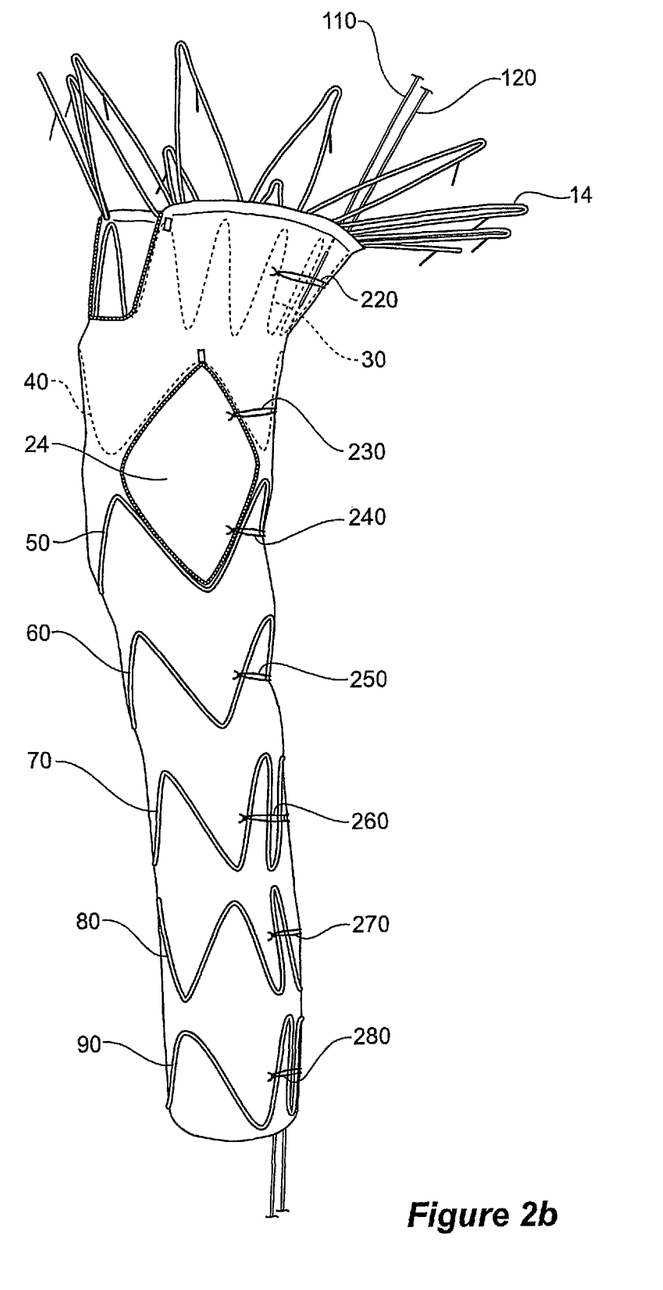
FIG. 2b shows the first embodiment of the invention as shown in FIG. 2a, but in a side view.
Figure 3:
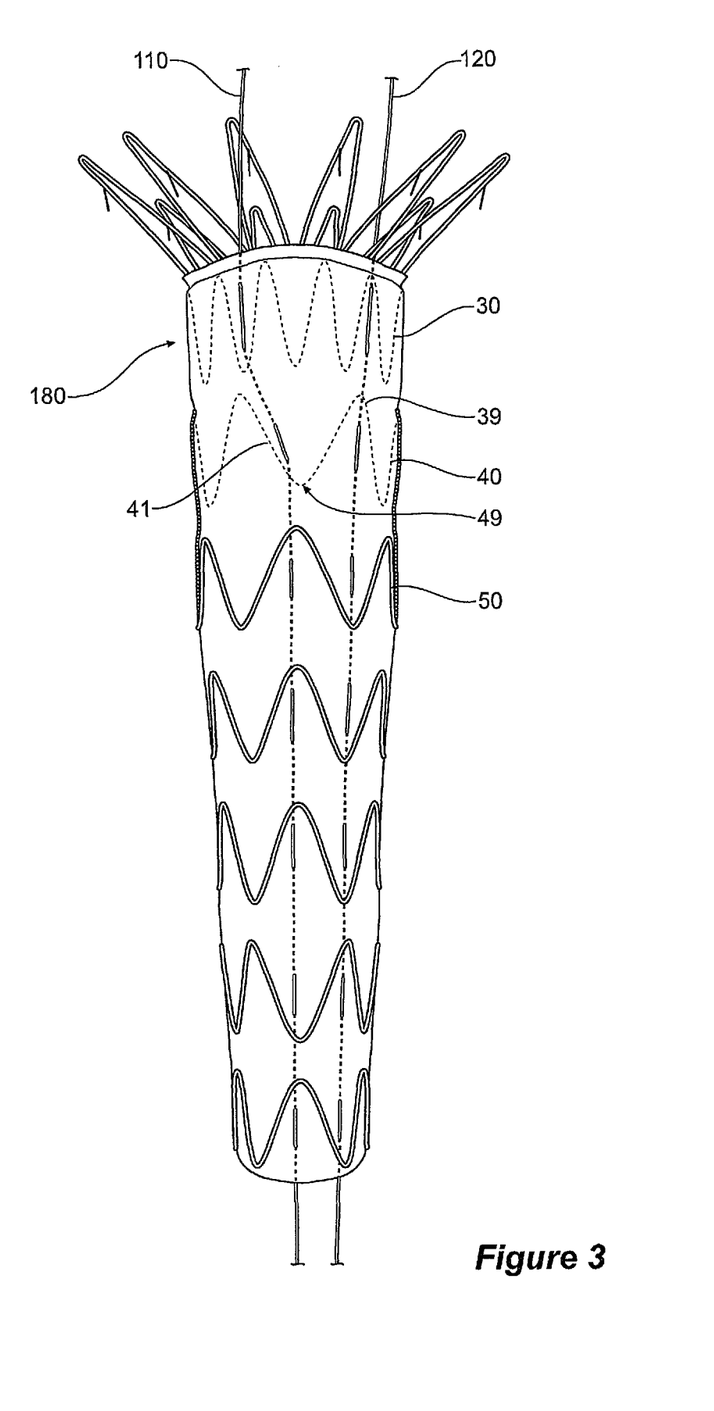

Referring now to FIGS. 2a, 2b and 3, a temporary diameter reduction constraint arrangement for a stent graft in combination with a stent graft according to a first embodiment of the invention is shown. The stent graft 10 has a proximal end 12 and a distal end 18 and comprises a biocompatible graft material tube 20 of a selected diameter. It has two internal stents 30, 40 and a plurality of external stents 50, 60, 70, 80, 90 along the length of its tubular body.

The internal stents 30, 40 are at the proximal end and act on a sealing zone also at the proximal end.

Fenestrations 24 and 25 are provided for allowing access to the renal arteries. This invention can facilitate matching the fenestrations 24 and 25 up with the renal arteries when the stent graft is deployed into an aorta. Methods of deployment of such a stent graft are described in PCT Patent Publication Number WO98/53761 entitled "A Prosthesis and a Method of Deploying a Prosthesis". These features and other features disclosed in PCT Patent Publication Number WO98/53761 could be used with the present invention and the disclosure of PCT Patent Publication Number WO98/53761 is herewith incorporated in its entirety into this specification.

Although the stent graft 10 shown is useable in aorta in the region of the renal arteries, the invention may be embodied in other stent grafts, which may or may not have fenestrations.

Again referring to FIGS. 2a, 2b and 3, it can be seen that there is a constraint arrangement comprising a primary release wire 110 extending longitudinally along the graft material tube 20 and a secondary release wire 120 also extending along the graft material tube 20. The primary and secondary release wires 110, 120 are simply threaded through the graft tube material 20 in the embodiment shown. In other embodiments, they may be attached in different ways. A plurality of loops of thread arranged in pairs engage with one or other of the primary and secondary release wires 110, 120 and engage around the portion of the stent graft circumferentially spaced a selected distance away from its release wire. For instance, an end constraint arrangement comprising four loops of thread arranged into a first pair 210 and second pair 220 of threads (sutures) is provided. The first pair 210 is engaged with the primary release wire 110 and the second pair 220 is engaged with the secondary release wire 120 as is shown most clearly in FIG. 2a.

Figure 7A:
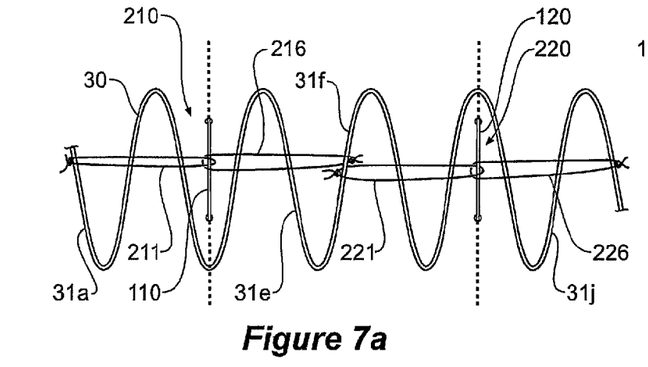
FIGS. 7a and 7b show how pairs of loops of thread are applied to a stent graft at a first location on the stent graft of FIGS. 2a, 2b and 3.
Figure 7B:
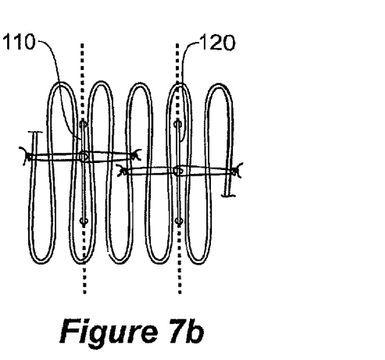

Referring now to FIGS. 7a and 7b the end constraint arrangement described above can be seen in more detail. FIG. 7b shows the loops of thread tightened and held in place by respective release wires 110 and 120. FIG. 7a shows that the first pair of threads 210 comprises a first thread 211 and a second thread 212. The second pair of threads 220 comprises a third thread 221 and a fourth thread 226.

Figure 6:
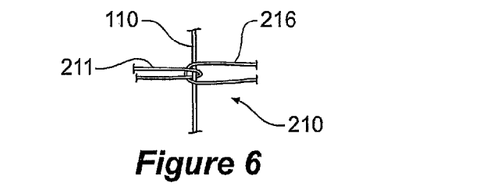
FIG. 6 shows how one pair of loops of thread, for use as diameter reducing ties, are engaged with a release wire.

An intermediate constraint arrangement comprising a fifth and sixth loop of thread 231 and 236 arranged in a third pair 230 is shown in FIGS. 7a and 7b. With the intermediate constraint arrangement, the third pair of threads 230 is only engaged with the primary release wire 110. The secondary release wire 120 is not used. The primary release wire 110 deviates towards the secondary release wire 120 so as to locate the intermediate constraint arrangement more centrally with respect to the end constraint arrangement described above. Further pairs of loops of threads 240, 250, 260, 270 and 280 are also shown in FIG. 2a. Threads pair 280, together with primary release wire 110, forms a distal end constraint arrangement. As is clear from FIG. 2a, the distal end constraint arrangement is substantially in-line with the intermediate constraint arrangement Referring to FIG. 6, a specific arrangement of threads 211 and 216 around release wire 110 is shown. With this arrangement, thread 211 is looped around the release wire 110 so as to provide engagement. In contrast, thread 216 is looped underneath thread 211 rather than being looped around release wire 110. This provides engagement with the release wire 110. The looped thread 216 relies on engagement with the release wire 110 and engagement with looped thread 211 to be held in place. With this arrangement, when the release wire 110 is withdrawn through the loop formed in thread 211, both threads 211 and 216 are released.

A method of temporarily reducing the diameter of at least a portion of a self-expanding stent graft in accordance with the invention will now be described.

Figure 5:
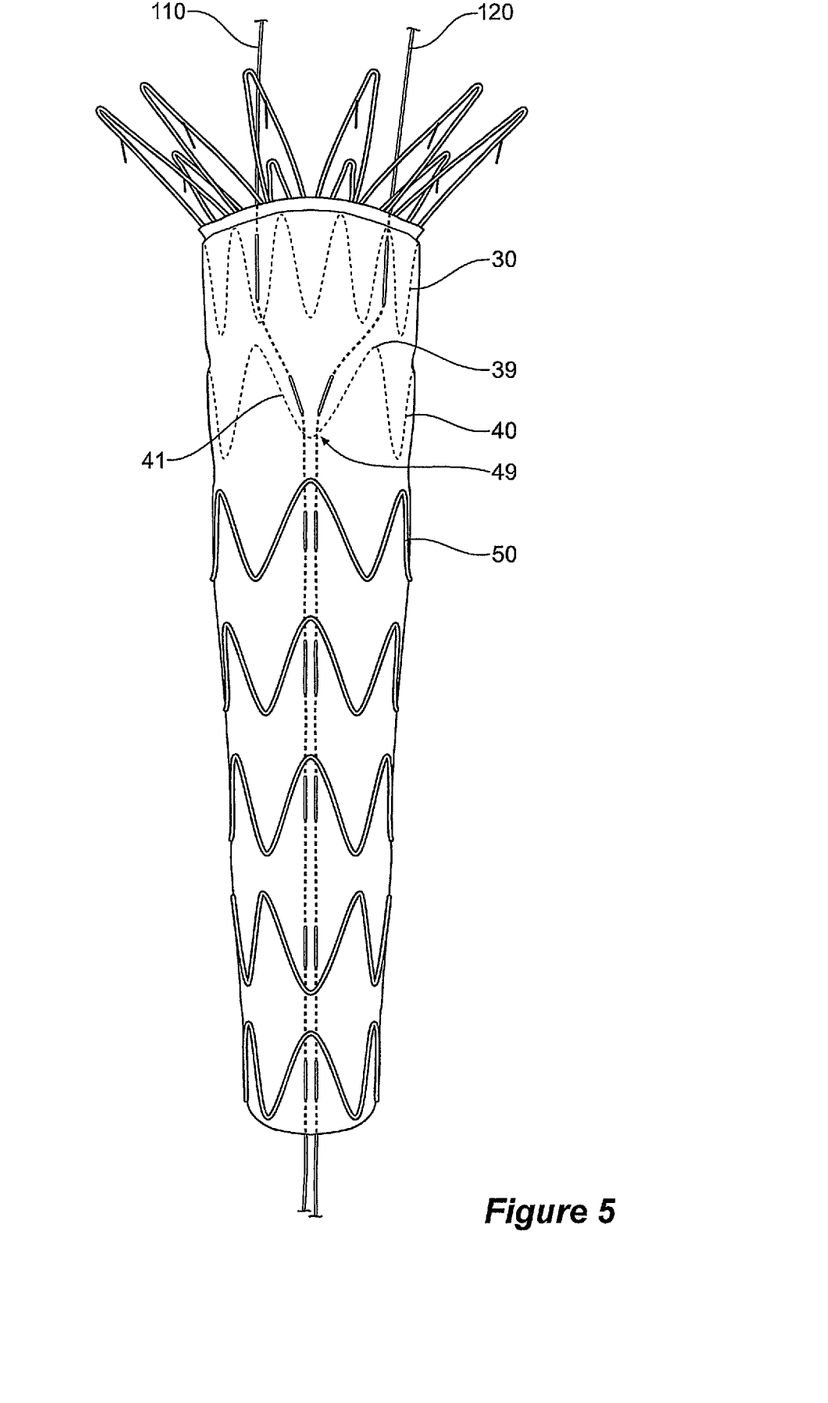
FIG. 5 shows a stage in the construction of the second embodiment of the invention as shown in FIG. 4.

The first stage is the placement and securing of release wires 110 and 120 longitudinally along the tubular body. FIGS. 3 and 5 show two alternatives for this step. In both of these assemblies, the release wires 110 and 120 and are stitched in and out of the tubular body. Stitches can be seen on the exterior of the tubular body in regions coinciding with the intermediate region of the struts of each of the exposed stents.

In the region designated as 180 in FIG. 2a, for instance, a suture 211 of the first pair 210, most clearly shown in FIGS. 7a and 7b is placed around the release wire 110 and extended across two struts of the zig-zag stent 30 to strut 31a where it is passed around the strut 31a and into the graft material tube 20 and pulled tight as shown in FIG. 7b. Similarly a suture 216 extended from the other direction from the release wire 110 for two struts is passed around a strut 31f and into the graft material of the graft material tube 20 and then pulled tight.

A second pair 220 of sutures 221 and 226 extending in opposite directions from release wire 120 are installed in a similar way to the first pair 210 to compress the other side.

Figure 4:
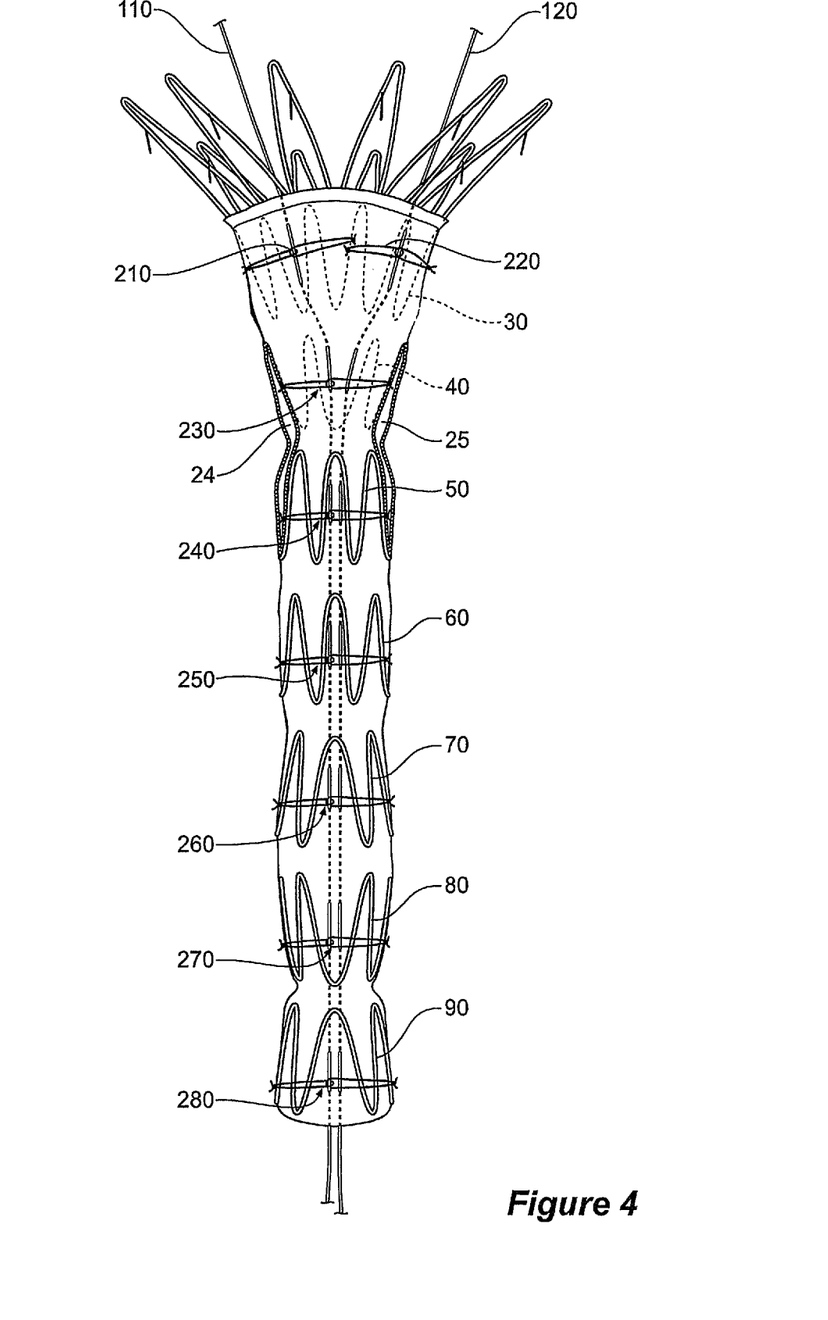
FIG. 4 shows a temporary diameter reduction constraint arrangement for a stent graft in combination with a stent graft according to a second embodiment of the invention in a front view.
Figure 8A:
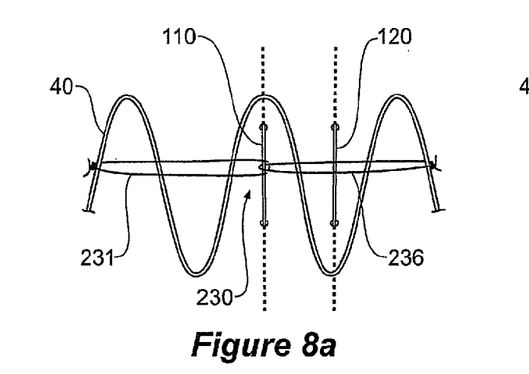
FIGS. 8a and 8b show how pairs of loops of thread are applied to a stent graft at a second location on the stent graft of FIGS. 2a, 2b and 3.
Figure 8B:
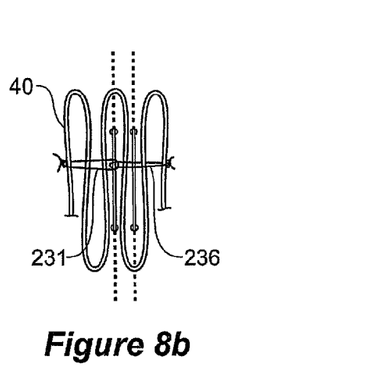
Figure 9A:
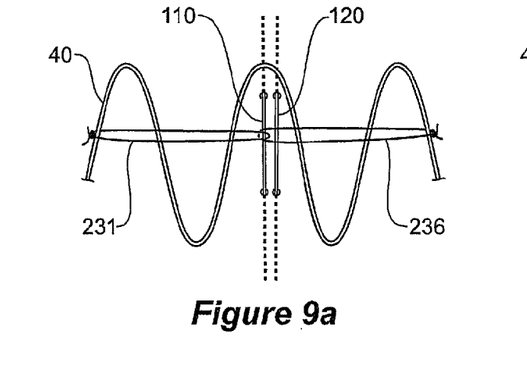
FIGS. 9a and 9b show how pairs of loops of thread are applied to a stent graft at a second location on the stent graft of FIGS. 4 and 5.
Figure 9B:
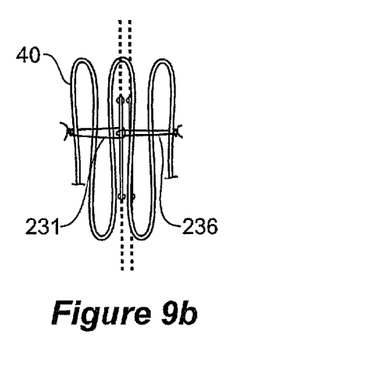

Referring now to FIG. 4, the temporary reductions in diameter in the region of the next strut 40 is shown. Only one pair, the third pair 230, of sutures 231, 236 and the release wire 110 is used for this as is most clearly shown in FIGS. 8a and 8b.

In the case of internal stents (e.g. stents 30 and 40), the sutures are inserted through the material of the tube 20 to go around the stents where they are knotted but otherwise remain outside of the tubular body.

The temporary restriction process is repeated with the next stent 50 (an exposed or external stent) and the remaining exposed stents 60, 70, 80, 90.

This gives the result as shown in FIGS. 2a and 2b where the diameter of the stent graft is considerably reduced. Diameter reducing ties may be either placed along the entire length of the stent graft so that the stent graft remains manoeuvrable after its partial release as discussed above or can be confined to only the parts of the stent graft that are larger in diameter than the vessel lumen into which it is to be placed.

Referring now to FIGS. 4 and 5, a temporary diameter reduction constraint arrangement for a stent graft in combination with a stent graft according to a second embodiment of the invention is shown. This embodiment is similar to the first embodiment shown in FIGS. 2a, 2b and 3, but both the first and the second release wires 110 and 120 converge.

Having two wires close together, as is achieved with both the first and second embodiment of the invention as can be seen in FIGS. 3 and 5 respectively, gives the stent graft more support and helps the stent graft sit straighter. This makes it easier to load onto a deployment device.

Figure 10:
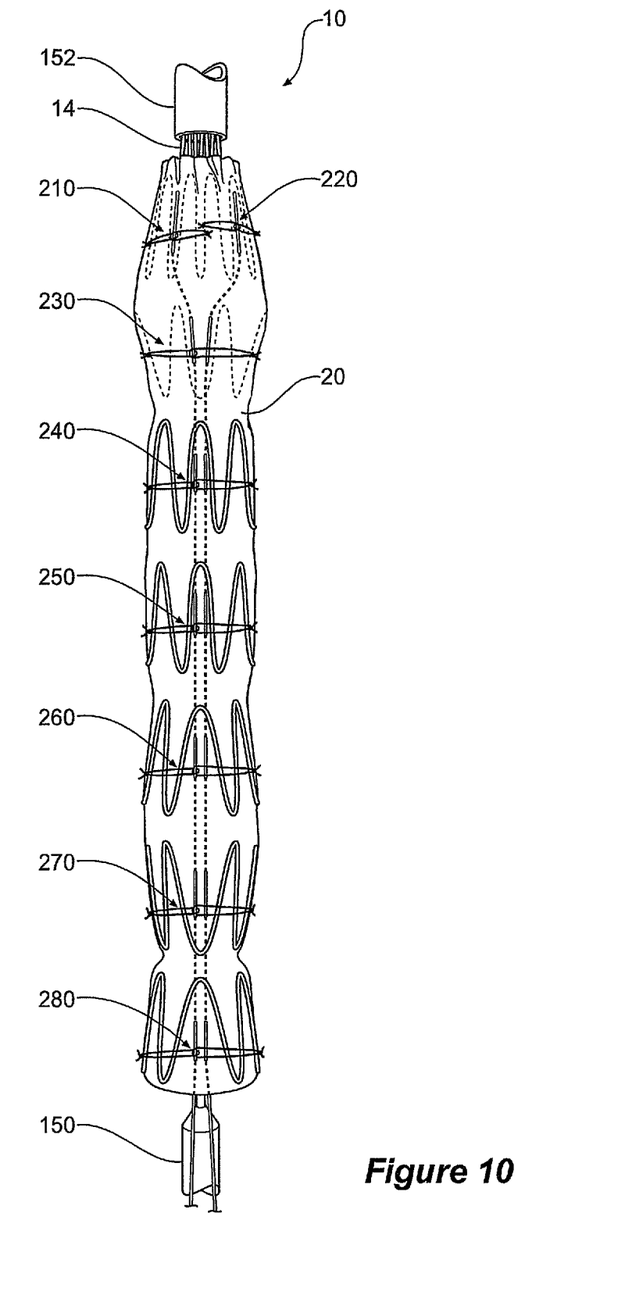
FIG. 10 shows the second embodiment of the invention on a delivery device.

FIG. 10 shows the stent graft of the second embodiment of the invention mounted onto a deployment device with a pusher catheter 150 at one end and a nose cone capsule 152 into which the proximally extending barbed stent 14 is received at the other end. At this stage a containing sheath has been withdrawn onto the pusher catheter so that the stent graft is partially expanded under the influence of self expanding stents but complete expansion has been prevented by the diameter reducing ties pairs 210, 220, 230, 240, 250, 260, 270 and 280.

The release wires 110 and 120 can be removed by the surgeon when (s)he no longer requires the diameter to be reduced. This can be when the stent graft is still mounted onto the deployment device so that the exposed stent 124 is still received in the capsule 152. After removal of the release wires 110 and 120, the sutures of the reducing tie pairs can remain on the outside of the stent graft. This does not cause problems as they do not interfere with blood flow and may assist with adhesion of the stent graft onto the wall of the aorta.

With the stent grafts described above, assembly is simplified since only one release wire 110 is used for stents 40, 50, 60, 70, 80 and 90. This simplification, while reducing labour, also reduces the likelihood of the ties not releasing correctly. More specifically, it is less likely that a person sewing or attaching the sutures around a single release wire will accidentally catch the fabric of the tubular body as compared to a person having to sewing sutures around a first release wire and then a second release wire. This is important because, if fabric is caught, then this is likely to inhibit deployment of the stent graft within a lumen.

With the embodiments illustrated, the expandable external stents 50, 60, 70, 80, 90 are nitinol (metal alloy of nickel and titanium) whereas the internal stents 30, 40 are stainless steel. Nitinol is super-elastic and stainless-steel is non-super elastic. In other embodiments, other suitable materials may be used.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A method of temporarily reducing a diameter of at least a portion of a self-expanding stent graft, the stent graft having a proximal end and a distal end and comprising a biocompatible graft material tube and a plurality of longitudinally spaced apart self-expanding stents fastened thereto, including at least an end stent and a plurality of intermediate stents, the method comprising the steps of:
   a) securing a primary release wire longitudinally along the stent graft;
   b) securing a secondary release wire longitudinally along the stent graft;
   c) tying an end constraint arrangement comprising four loops of thread arranged into a first pair and a second pair, the first pair engaged with the primary release wire and the second pair engaged with the secondary release wire; and
   d) tying an intermediate constraint arrangement comprising two loops of thread arranged into a third pair, the third pair engaged with the primary release wire, wherein,
   the primary release wire deviates towards the secondary release wire.

2. The method as claimed in claim 1 comprising the step of:
   tying a plurality of intermediate constraint arrangements, each intermediate constraint arrangement comprising two loops of thread arranged into pairs, the pairs engaged with the primary release wire, so as to reduce the diameter of the stent graft along an entire length of the stent graft.

3. The method as claimed in claim 2 wherein the securing steps comprise threading the release wires through the graft material tube.

4. The method claimed in claim 3 wherein the securing steps comprise tying the primary release wire so as to deviate towards the secondary release wire.

5. The method claimed in claim 4 wherein the securing steps comprise tying the secondary release wire so as to deviate towards the primary release wire.

6. The method as claimed in claim 5 wherein the deviation of the primary and secondary release wires toward each other is symmetrical.

7. The method as claimed in claim 6 wherein the end constraint arrangement constrains a sealing stent at the proximal end of the stent graft.

8. The method as claimed as claimed in claim 7 wherein the steps further comprise tying a distal end constraint arrangement to be substantially in-line with the intermediate constraint arrangement.

9. A method of temporarily reducing a diameter of at least a portion of a self-expanding stent graft, the stent graft having a proximal end and a distal end and comprising a biocompatible graft material tube and a plurality of longitudinally spaced apart self-expanding stents fastened thereto, including at least an end stent and a plurality of intermediate stents, the method comprising the steps of:
   a) securing a primary release wire longitudinally along the stent graft;
   b) securing a secondary release wire longitudinally along the stent graft;
   c) tying an end constraint arrangement comprising four loops of thread arranged into a first pair and second pair, the first pair engaged with the primary release wire and the second pair engaged with the secondary release wire; and
   d) tying an intermediate constraint arrangement comprising two loops of thread arranged into a third pair, the third pair engaged with the primary release wire, wherein,
   the primary release wire deviates towards the secondary release wire and the secondary release wire deviates toward the primary release wire.

10. The method as claimed in claim 9 comprising the step of:
    tying a plurality of intermediate constraint arrangements, each intermediate constraint arrangement comprising two loops of thread arranged into pairs, the pairs engaged with the primary release wire, so as to reduce the diameter of the stent graft along an entire length of the stent graft.

11. The method as claimed in claim 10 wherein the securing steps comprise threading the release wires through the graft material tube.

12. The method as claimed in claim 9 wherein the deviation of the primary and secondary release wires toward each other is symmetrical.

13. The method as claimed in claim 9 wherein the end constraint arrangement constrains a sealing stent at the proximal end of the stent graft.

14. The method as claimed as claimed in claim 9 wherein the steps further comprise tying a distal end constraint arrangement to be substantially in-line with the intermediate constraint arrangement.

15. A method of temporarily reducing a diameter of at least a portion of a self-expanding stent graft, the stent graft having a proximal end and a distal end and comprising a biocompatible graft material tube and a plurality of longitudinally spaced apart self-expanding stents fastened thereto, including at least an end stent and a plurality of intermediate stents, the method comprising the steps of:
   a) securing a primary release wire longitudinally along the stent graft;
   b) securing a secondary release wire longitudinally along the stent graft;
   c) tying an end constraint arrangement comprising four loops of thread arranged into a first pair and second pair, the first pair engaged with the primary release wire and the second pair engaged with the secondary release wire; and
   d) tying a plurality of intermediate constraint arrangements, each intermediate constraint arrangement comprising two loops of thread arranged into pairs, the pairs engaged with the primary release wire, so as to reduce the diameter of the stent graft along an entire length of the stent graft,
   wherein,
   the primary release wire deviates towards the secondary release wire and the secondary release wire deviates toward the primary release wire.

16. The method as claimed in claim 15 wherein the securing steps comprise threading the release wires through the graft material tube.

17. The method as claimed in claim 16 wherein the deviation of the primary and secondary release wires toward each other is symmetrical.

18. The method as claimed in claim 15 wherein the end constraint arrangement constrains a sealing stent at the proximal end of the stent graft.

19. The method as claimed as claimed in claim 17 wherein the steps comprise tying a distal end constraint arrangement to be substantially in-line with the intermediate constraint arrangement.

20. The method as claimed in claim 18 wherein the steps further comprise tying the end constraint arrangement around a strut of the stent graft.

* * * * *